(12) United States Patent
Lin et al.

(10) Patent No.: US 8,729,026 B2
(45) Date of Patent: May 20, 2014

(54) METHOD FOR INHIBITING AUTOPHAGY OF MOTOR NEURONS

(71) Applicant: China Medical University, Taichung (TW)

(72) Inventors: Shinn-Zong Lin, Taichung (TW);
Horng-Jyh Harn, Taichung (TW);
Tzyy-Wen Chiou, Taichung (TW);
Kuo-Wei Hsueh, Taichung (TW)

(73) Assignee: China Medical University, Taichung (TW)

( * ) Notice: Subject to any disclaimer, the term of this patent is extended or adjusted under 35 U.S.C. 154(b) by 0 days.

(21) Appl. No.: 13/693,653

(22) Filed: Dec. 4, 2012

(65) Prior Publication Data

US 2014/0045765 A1 Feb. 13, 2014

(30) Foreign Application Priority Data

Aug. 10, 2012 (TW) .............................. 101129160 A

(51) Int. Cl.
*A61K 38/06* (2006.01)
*A61K 31/192* (2006.01)

(52) U.S. Cl.
CPC ............. *A61K 31/192* (2013.01); *A61K 38/063* (2013.01)
USPC ....................................................... 514/17.9

(58) Field of Classification Search
CPC ..................................................... A61K 31/00
See application file for complete search history.

(56) References Cited

U.S. PATENT DOCUMENTS

| | | | | |
|---|---|---|---|---|
| 7,455,861 | B2 * | 11/2008 | Luo et al. ....................... | 424/725 |
| 2009/0176873 | A1 | 7/2009 | Fowler et al. | |
| 2010/0298427 | A1 | 11/2010 | Fowler et al. | |

FOREIGN PATENT DOCUMENTS

| | | |
|---|---|---|
| CN | 101184484 | 5/2008 |
| WO | 2008/017491 A1 | 2/2008 |

OTHER PUBLICATIONS

Acevedo-Arozena et al., A comprehensive assessment of the SOD1G93A low-copy transgenic mouse, which models human amyotrophic lateral sclerosis, 2011, Disease Models & Mechanisms 4:686-700.*
Tsai et al., The natural compound n-butylidenephthalide derived from Angelica sinensis inhibits malignant brain tumor growth in vitro and in vivo, 2006, Journal of Neurochemistry 99:1251-1262.*
Ko et al., The Selective Antianginal Effect without Changing Blood Pressure of Butylidenephthalide in Conscious Rats, 1998, Planta Medica 64:229-232.*
Tian, F et al., "In vivo optical imaging of a motor neuron autophagy in a mouse model of amyotrophic lateral sclerosis", Sep. 2011, pp. 985-992, vol. 7:9, Autophagy.
Del Signore, S et al., "Combined riluzole and sodium pheriylbutyrate therapy in transgenic amyotrophic lateral sclerosis mice", 2009, pp. 85-94, vol. 10, Amyotropic Lateral Sclerosis.
Zhang, X, et al., "Rapamycin treatment augments motor neuron degeneration in SOD1G93A mouse model of amyotrophic lateral sclerosis". Autophagy, vol. 7, Issue 4, Apr. 2011, pp. 421-425.
Morimoto, N, et al., "Increased autophagy in transgenic mice with a G93A mutant SOD1 gene". Brain research, vol. 1167, Sep. 5, 2007, pp. 112-117.
Ohta, Y. et al., "Neuroprotective and Angiogenic Effects of Bone Marrow Transplantation Combined With Granulocyte Colony-Stimulating Factor in a Mouse Model of Amyotrophic Lateral Sclerosis", Cell Medicine, Part B of Cell Transplantation. vol. 2, No. 2, Feb. 2011, pp. 69-83.
Fornai, F. et al., "Lithium delays progression of amyotrophic lateral sclerosis", PNAS, vol. 105, No. 6, Feb. 2008, pp. 2052-2057.
Sekiya et al., "Distribution, metabolism and excretion of butylidenephthalide of Ligustici chuanxiong rhizoma in hairless mouse after dermal application", Journal of Ethnopharmacology, 71 (2000), pp. 401-409.
Zuo et al., "Identification of the absorbed compounds and metabolites in rat plasma after oral administration of Rhizoma Chuanxiong decoction by HPLC-ESI-MS/MS", Journal of Pharmaceutical and Biomedical Analysis, 56 (2011), pp. 1046-1056.

* cited by examiner

*Primary Examiner* — John Ulm
(74) *Attorney, Agent, or Firm* — Ping Wang; Andrews Kurth LLP

(57) ABSTRACT

A method for inhibiting the autophagy of motor neurons in a subject is provided. The method comprises administrating to the subject an effective amount of an active ingredient selected from the group consisting of a compound of formula (I), a pharmaceutically acceptable salt of the compound, a pharmaceutically acceptable ester of the compound and combinations thereof:

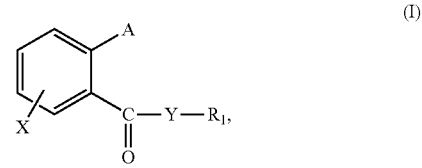

wherein A is a C1-C5 alkyl optionally having one or more unsaturated bonds and optionally being substituted by one or more substituents selected from a group consisting of —OH, =O and C1-C3 alkyl; X is H, —OH,

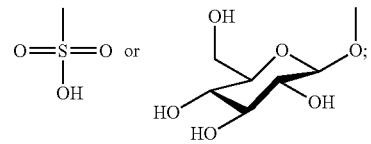

Y is O or S and can optionally combine with A to form a five-membered ring; and $R_1$ is H or a substituted or unsubstituted C1-C20 alkyl, wherein one or more —$CH_2$— of the C1-C20 alkyl are optionally being replaced by —NH— or —O—.

9 Claims, 8 Drawing Sheets

Control group (untreated)

Experimental group (BP, 500 mg/kg-body weight)

METHOD FOR INHIBITING AUTOPHAGY OF MOTOR NEURONS

CLAIM FOR PRIORITY

This application claims the benefit of Taiwan Patent Application No. 101129160, filed on Aug. 10, 2012, in the Taiwan Intellectual Property Office, the disclosure of which is incorporated herein in its entirety by reference.

BACKGROUND OF THE INVENTION

1. Field of the Invention

The present invention relates to a method for inhibiting the autophagy of motor neurons, especially for delaying the onset of motor neuron degenerative diseases and/or curing motor neuron degenerative diseases.

2. Descriptions of the Related Art

A neuron, also known as a nerve cell, is one of the structural and functional units of the nervous system of the organism. Neurons can transmit messages to other cells by chemical and electrical signals. Neurons can vary in shape and size, and the diameters of neurons may range from about 4 μm to about 100 μm. The structure of a neuron can be roughly divided into three parts: a cell body, dendrites, and an axon, wherein dendrites can transmit signals into cell bodies, and axons can transmit signals out from cell bodies.

Neurons can be classified into three types depending on the direction of their signal transduction and functions: sensory neurons, motor neurons and interneurons, wherein a motor neuron is a nerve cell controlling the body activities of an organism. In general, motor neurons in the brain are known as upper motor neurons, while motor neurons in the brain stem and the spinal cord are known as lower motor neurons. Functional disorders caused by the degeneration of motor neurons may result in motor neuron degenerative diseases, such as amyotrophic lateral sclerosis (ALS), myasthenia gravis, myasthenia, muscular atrophy, muscular dystrophy, multiple sclerosis, multiple-system atrophy, spinal muscular dystrophy, etc. Patients suffering from the aforesaid motor neuron degenerative diseases will gradually show symptoms such as muscle weakness, atrophy, trembling, cramping rigidity, which may lead to difficulty speaking, difficulty swallowing, and respiratory failure.

The real cause of motor neuron degenerative diseases is still uncertain to date. However, research has shown that the possible causes of the disease include neuronal death caused by excessive autophagy stimulated by the accumulation of superoxide anions, autoimmune disorder, excessive neuronal excitation (e.g., excessive accumulation of glutamates), excessive oxidation, and heredity, etc. The medicines presently used in clinic to treat motor neuron degenerative diseases include glutamate antagonists such as Riluzole, antioxidants such as vitamin E, neurotrophic factors, immune modulators, etc. However, the aforesaid medicines usually do not have significant therapeutic effect or may only lengthen the life of the patients for 3 to 6 months. Therefore, there is still a need for a medicine to delay the onset of motor neuron degenerative diseases and/or cure motor neuron degenerative diseases.

The inventors of the present invention found that the compound of formula (I) of the present invention can be used to inhibit the autophagy of motor neurons and decrease motor neuronal death, thereby, delaying the onset of motor neuron degenerative diseases and/or curing motor neuron degenerative diseases.

SUMMARY OF THE INVENTION

An objective of the present invention is to provide a method for inhibiting the autophagy of motor neurons in a subject, comprising administrating to the subject an effective amount of an active component selected from the group consisting of a compound of formula (I), a pharmaceutically acceptable salt of the compound of formula (I), a pharmaceutically acceptable ester of the compound of formula (I), and combinations thereof:

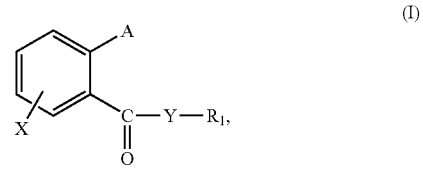

(I)

wherein, A is a C1-C5 hydrocarbyl group optionally having one or more unsaturated bonds, and is optionally substituted by one or more substituents selected from the group consisting of —OH, =O, and C1-C3 hydrocarbyl group;
X is H, —OH,

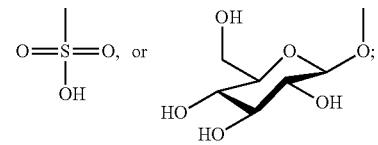

Y is O or S and optionally bonds with A to form a five-membered ring; and
$R_1$ is H or a substituted or unsubstituted C1-C20 hydrocarbyl group, wherein one or more —$CH_2$— in the hydrocarbyl group are optionally replaced by —NH— or —O—.

Another objective of the present invention is to use the aforesaid active component in the manufacture of a medicament for inhibiting the autophagy of motor neurons.

The detailed technology and the preferred embodiments implemented for the present invention will be described in the following paragraphs for people skilled in the field to well appreciate the features of the claimed invention.

DETAILED DESCRIPTION OF THE INVENTION

Figure 1A:
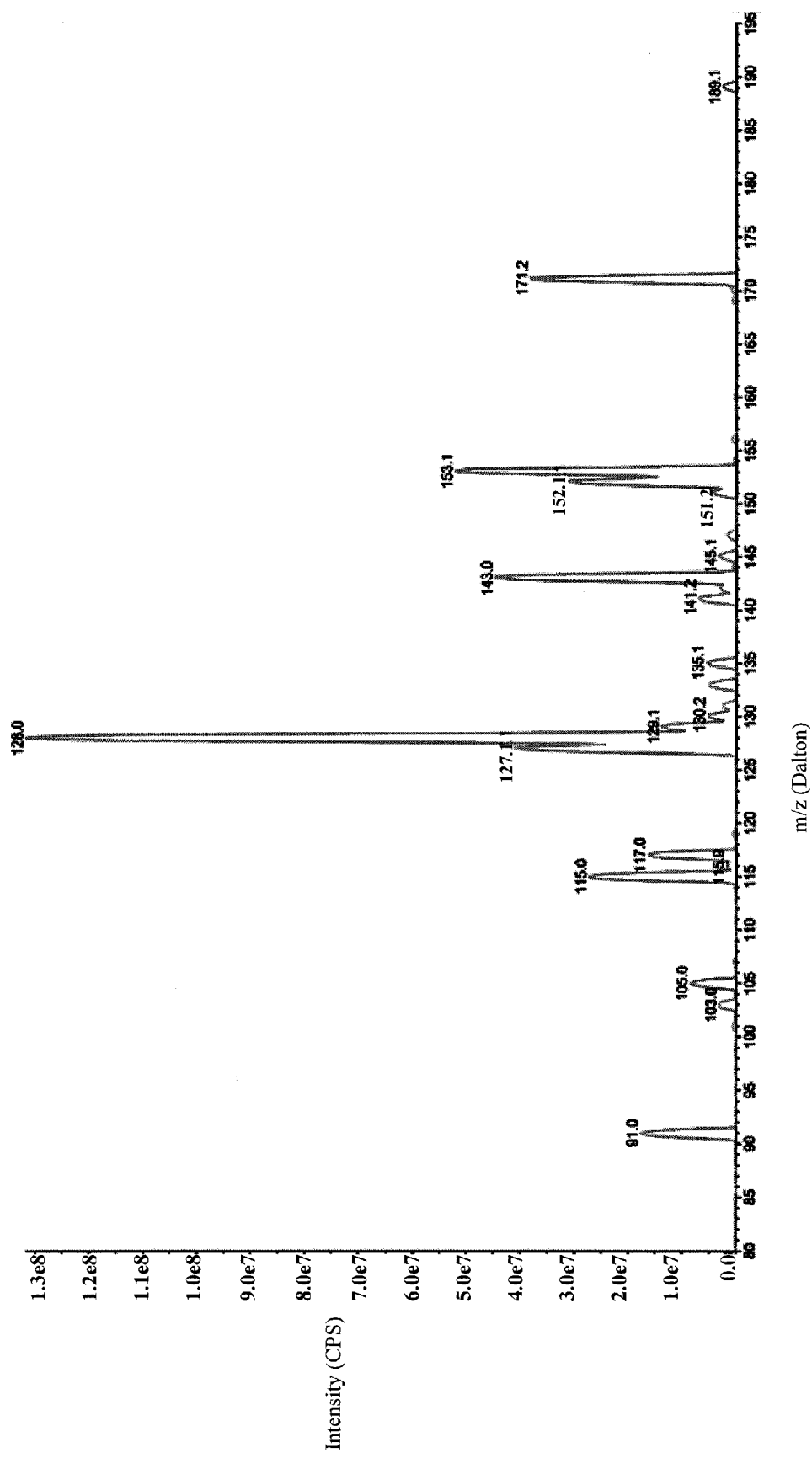
FIG. 1A is a mass spectrum of a mixture of butylidenephthalide and human hepatic microsomes analyzed by LC-MS/MS.

The following will describe some embodiments of the present invention in detail. However, without departing from the spirit of the present invention, the present invention may be embodied in various embodiments and should not be limited to the embodiments described in the specification. In addition, unless otherwise state herein, the expressions "a," "the," or the like recited in the specification of the present invention (especially in the claims) should include both the singular and the plural forms. Furthermore, the term "effective amount" used in this specification refers to the amount of the compound that can at least partially alleviate the condition that is being treated in a suspected subject when administered to the subject. The term "subject" used in this specification refers to a mammalian, including human and non-human animals.

Autophagy is an important mechanism for regulating cell growth, cell homeostasis and cell death, involving the degradation of a cell's own organelles or other materials through intracellular lysosomes of cells. However, as indicated above, it has been known that the excessive autophagy of motor neurons is one of the causes of motor neuron degenerative diseases. Therefore, if the autophagy of motor neurons can be inhibited, then motor neuronal death can be alleviated so as to treat motor neuron degenerative diseases.

The inventors of the present invention have found that the following compound (1) can effectively inhibit the autophagy of motor neurons, and thus, it can be used to delay the onset of motor neuron degenerative diseases and/or cure motor neuron degenerative diseases.

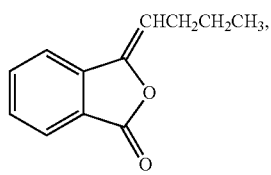
(1)

Compound (1), also known as butylidenephthalide (BP), comprises two isomers in its natural state, (Z)-butylidenephthalide (cis-butylidenephthalide) and (E)-butylidenephthalide (trans-butylidenephthalide).

It has been confirmed that after butylidenephthalide is metabolized by phase I metabolism or phase II metabolism in the liver of an organism, one or more of the following compounds (2) to (14) will be produced:

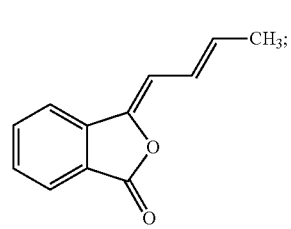
(2)

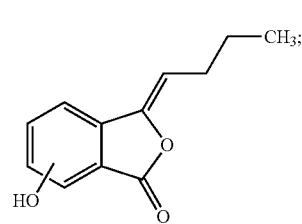
(3)

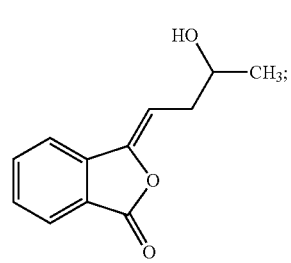
(4)

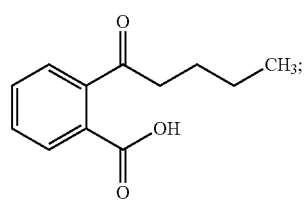
(5)

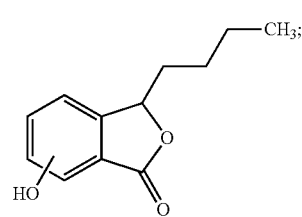
(6)

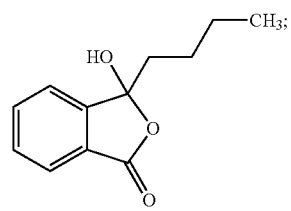
(7)

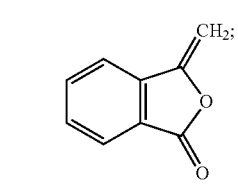
(8)

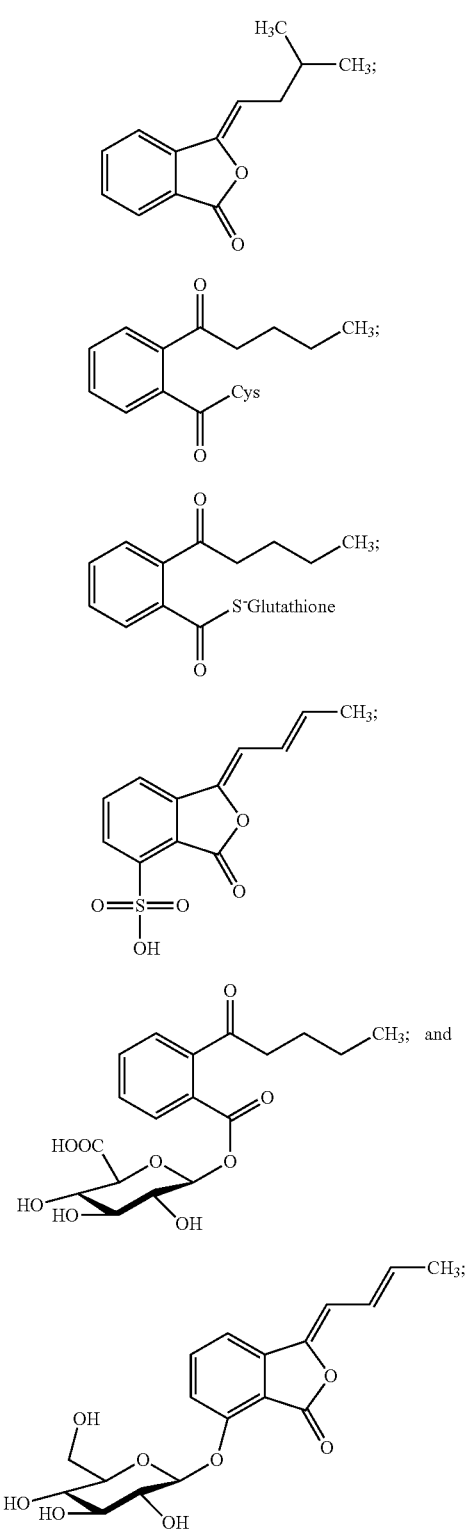

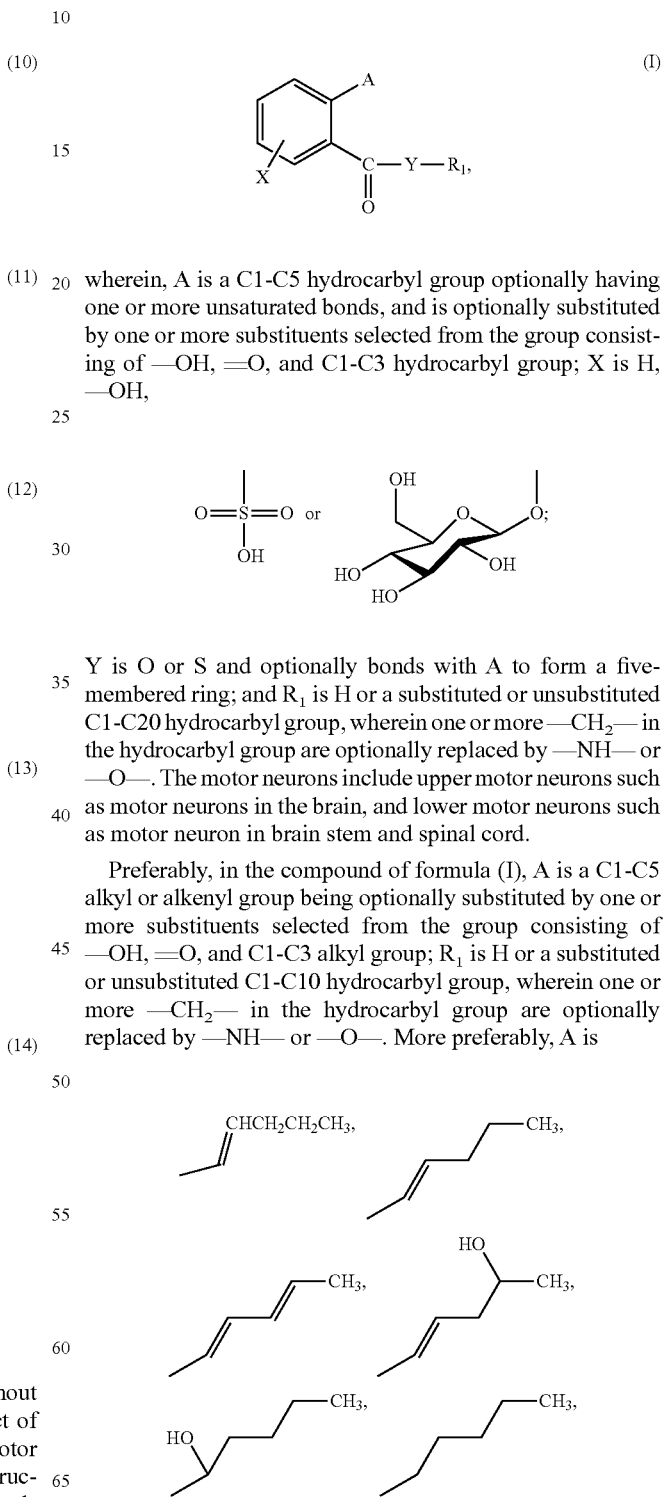

wherein the Cys in compound (10) refers to cysteine. Without being limited by the theory, it is believed that the effect of butylidenephthalide on inhibiting the autophagy of motor neurons in the organism originates from the common structural part of the chemical structures of the above compounds (2) to (14).

Therefore, the present invention provides a method for inhibiting the autophagy of motor neurons in a subject, comprising administrating to the subject an effective amount of an active component selected from the group consisting of a compound of formula (I), a pharmaceutically acceptable salt of the compound of formula (I), a pharmaceutically acceptable ester of the compound of formula (I), and combinations thereof:

wherein, A is a C1-C5 hydrocarbyl group optionally having one or more unsaturated bonds, and is optionally substituted by one or more substituents selected from the group consisting of —OH, =O, and C1-C3 hydrocarbyl group; X is H, —OH, Y is O or S and optionally bonds with A to form a five-membered ring; and $R_1$ is H or a substituted or unsubstituted C1-C20 hydrocarbyl group, wherein one or more —$CH_2$— in the hydrocarbyl group are optionally replaced by —NH— or —O—. The motor neurons include upper motor neurons such as motor neurons in the brain, and lower motor neurons such as motor neuron in brain stem and spinal cord.

Preferably, in the compound of formula (I), A is a C1-C5 alkyl or alkenyl group being optionally substituted by one or more substituents selected from the group consisting of —OH, =O, and C1-C3 alkyl group; $R_1$ is H or a substituted or unsubstituted C1-C10 hydrocarbyl group, wherein one or more —$CH_2$— in the hydrocarbyl group are optionally replaced by —NH— or —O—. More preferably, A is -continued

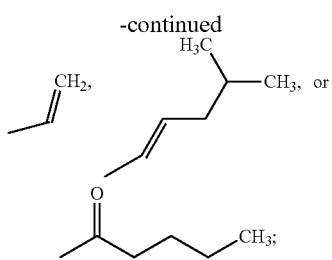

and R₁ is H,

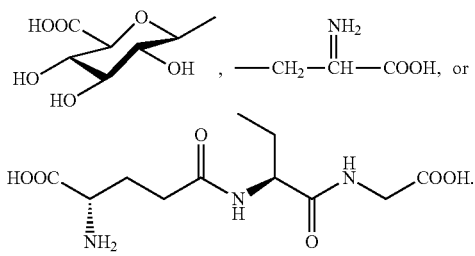

In one embodiment of the method of the present invention, the compound of formula (I) is selected from the group consisting of the above compounds (1) to (14). The compound of formula (I) is preferably compound (1) (i.e., butylidenephthalide), and is more preferably a compound of the following formula (i.e., (Z)-butylidenephthalide):

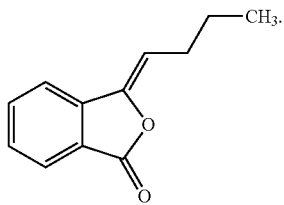 [SMILES: CCC/C=C1\OC(=O)c2ccccc21]

The method of the present invention can inhibit the autophagy of motor neurons and can alleviate neuronal death, and thus, it can be used to delay the onset of motor neuron degenerative diseases and/or cure motor neuron degenerative diseases. The motor neuron degenerative diseases comprise any diseases related to the autophagy of motor neurons, including but not limited to amyotrophic lateral sclerosis, myasthenia gravis, myasthenia, muscular atrophy, muscular dystrophy, multiple sclerosis, multiple system atrophy, spinal muscular atrophy, etc.

In one embodiment, the method of the present invention is used for curing amyotrophic lateral sclerosis. The patients of amyotrophic lateral sclerosis will gradually show muscular atrophy, which usually causes quadriplegia, difficulty swallowing and even respiratory failure in 2 to 5 years. Researches have shown that amyotrophic lateral sclerosis may be related to excessive neuronal excitation (e.g., excessive accumulation of glutamates). Therefore, at present, the glutamate antagonist, such as Riluzole, is usually used in clinic to cure motor neurodegenerative diseases to increase the survival rate of the patients. As compared with Riluzole, the active component of the present invention can more effectively delay the onset of motor neuron degenerative diseases and/or cure motor neuron degenerative diseases by inhibiting the autophagy of motor neurons, and thereby, can increase the survival rate of amyotrophic lateral sclerosis patients.

In the method of the present invention, the aforesaid active component can be administrated as a pharmaceutical composition. The pharmaceutical composition can be manufactured into a medicament of any suitable form for administration. For example, but not limited thereby, the pharmaceutical composition can be manufactured into a medicament with a form suitable for oral administration, subcutaneous injection, nasal administration or intravenous injection. Because a medicament for oral administration is convenient for patients to take regularly by themselves, it is preferably that the pharmaceutical composition is manufactured into a medicament in a form suitable for oral administration. Depending on the form and purpose of the medicament, the pharmaceutical composition may further comprise a pharmaceutically acceptable carrier.

For manufacturing a medicament suitable for oral administration, the pharmaceutical composition can comprise a pharmaceutically acceptable carrier which has no adverse influence on the activity of the active component comprised therein, such as a solvent, oily solvent, diluent, stabilizer, absorption delaying agent, disintegrant, emulsifier, antioxidant, binder, lubricants, moisture absorbent, etc. The medicament can be in a form suitable for oral administration, such as a tablet, a capsule, a granule, powder, a fluid extract, a solution, syrup, a suspension, an emulsion, a tinctures, etc.

As for a medicament suitable for subcutaneous or intravenous injection, the pharmaceutical composition may comprise one or more components, such as an isotonic solution, a saline buffer solution (e.g., a phosphate buffer solution or a citrate buffer solution), a solubilizer, an emulsifier, other carriers, etc., so as to manufacture the medicament as an intravenous injection, an emulsion intravenous injection, a powder injection, a suspension injection, a powder-suspension injection, etc.

In addition to the above adjuvants, the pharmaceutical composition may comprise other addatives, such as a flavoring agent, a toner, a coloring agent, etc. to enhance the taste and visual appeal of the resultant medicament. To improve the storability of the resultant medicament, the pharmaceutical composition may also comprise a suitable amount of a preservative, a conservative, an antiseptic, an anti-fungus reagent, etc. Furthermore, the pharmaceutical composition may comprise one or more other active components, such as an antioxidant (e.g., vitamin E), neurotrophic factor, immune modulator, etc., to further enhance the effect of the method of the present invention or increase the application flexibility and adaptability for the method, as long as the other active components have no adverse effect on the compound of formula (I) or its salt and ester derivatives.

Depending on the requirements of the subject, the compound of formula (I) and/or its salt and ester derivatives can be applied with various administration frequencies, such as once a day, several times a day or once for days, etc. For example, when applied to the human body for inhibiting the autophagy of motor neurons, the dosage of the compound of formula (I) and/or its salt and ester derivatives is about 30 mg (as the compound of formula (I))/kg-body weight to about 2000 mg (as the compound of formula (I))/kg-body weight per day, and preferably is about 100 mg (as the compound of formula (I))/kg-body weight to about 1000 mg (as the compound of formula (I))/kg-body weight per day, wherein the unit "mg/kg-body weight" means the dosage required per kg-body weight. However, for patients with acute conditions, the dosage can be increased to several times or several tens of times, depending on the practical requirements. In one embodiment using the method of the present invention to cure amyotrophic lateral sclerosis, the active component is (Z)-butylidenephthalide and its dosage is about 500 mg/kg-body weight.

The present invention also provides the use of the compound of formula (I) and/or its pharmaceutically acceptable salt(s) and ester(s) in the manufacture of a medicament for inhibiting the autophagy of motor neurons. By inhibiting the autophagy of motor neurons, the medicament can be used to delay the onset of motor neuron degenerative diseases and/or cure motor neuron degenerative diseases, such as amyotrophic lateral sclerosis, myasthenia gravis, myasthenia, muscular atrophy, muscular dystrophy, multiple sclerosis, multiple-system atrophy, spinal muscular dystrophy, and combinations thereof. The formulations and dosages of the medicament, and the other components optionally comprised therein are all in line with the above descriptions.

The present invention will be further illustrated in details with specific examples as follows. However, the following examples are provided only for illustrating the present invention, and the scope of the present invention is not limited thereby.

EXAMPLE

Example 1

Identification of the Metabolites of butylidenephthalide

It has been known that the medicine metabolic pathway within an organism's liver can be primarily divided into phase I and phase II metabolism. Phase I metabolism occurs mainly by the redox reaction or hydrolysis reaction of medicine, and phase II metabolism occurs mainly by cytochrome P450 (CYP450) monoxygenase system. This example simulated the phase I and II metabolism of butylidenephthalide that occur within an organism's liver by respectively mixing butylidenephthalide with hepatic microsomes or cryopreserved hepatocytes in vitro, and the products in the reaction solution were analyzed by liquid chromatograph-tandem mass spectrometer (LC-MS/MS) to identify the metabolites and the metabolic profile. The experimental steps were as follows:

(1) Phase I Metabolism Assay

Butylidenephthalide (2 mM) was mixed respectively with $K_3PO_4$ buffer solution (100 mM, pH7.4) containing human, rats or dogs hepatic micrsomes (0.5 mg/mL). The mixture was maintained at 37° C. for 10 minutes, and then pre-warmed cofactors (NADPH (2 mM) and $MgCl_2$ (3 mM)) were added thereto and the mixture was incubated at 37° C. for 60 minutes. Thereafter, 3-fold volume of acetonitrile containing 0.1% formic acid was added to the mixture to terminate the reaction. The mixture was centrifuged at 13000 rpm for 5 minutes, and the supernatant was then collected and analyzed by LC-MS/MS to identify the metabolites.

(2) Phase II Metabolism Assay

William's E medium containing $5 \times 10^5$ thawed human, rat or dog hepatocytes were respectively added into a 12-well culture dish, and the cells were cultured for 6 hours. Then, 0.5 mL of butylidenephthalide (50 μM) was added into the culture dish. After the cells were incubated at 37° C., 95% relative humidity and 5% $CO_2$ for 6 hours, 2 mL of acetonitrile (100%) was added to terminate the reaction. The sample was collected, mixed adequately, and centrifuged at 45000 g, 4° C. for 10 minutes. The supernatant was then collected, dried, and analyzed by LC-MS/MS to identify the metabolites.

(3) LC-MS/MS Analysis

The samples obtained from (1) and (2) were separately dissolved in acetonitrile/0.1% formic acid, centrifuged at 45000 g, 4° C. for 10 minutes. Then, the aliquots (20 μl) of each sample was injected into an autosampler vial (Agilent Technologies, USA) of a LC-MS/MS system to perform LC-MS/MS analysis. The LC-MS/MS system comprises an ABSCIEX 5500 Q TRAP™ system with 1200SL HPLC system (Agilent Technologies, USA), a HPLC column (Symmetry® C18, 3.5 4.6×75 mm), and a autosampler (Agilent Technologies, USA). A two-solvent system (solvent A: 0.1% formic acid; solvent B: methanol containing 0.1% formic acid) was used to perform HPLC at a flow rate of 0.8 mL/min. The HPLC gradient system was set as follows: 0 to 2 minutes held at 10% solvent B; 2 to 7 minutes with a gradient from 10% to 95% solvent B; 7 to 12 minutes held at 95% solvent B; 12 to 14 minutes with a gradient from 95% to 10% solvent B; 14 to 20 minutes held at 10% solvent B; and the retention time of HPLC analysis is 20 minutes. The mass spectrometry analysis was performed in positive ion electrospray ionization (+ESI) mode at 5.5 kV, 550° C., and $N_2$ (nitrogen) was used as an auxiliary gas. The most intense peaks in the LC-MS/MS spectrum and the mass-shifted peaks in the LC-MS/MS spectrum of each sample as compared to butylidenephthalide spectrum were analyzed by LightSight™ Software for determining the metabolites in the samples and identifying the biotransformation pathway and metabolic profile of butylidenephthalide in an organism. The results are shown in Table 1, Table 2, FIG. 1A, FIG. 1B and FIG. 1C.

FIG. 1A shows the fragment product spectrum of the mixture of butylidenephthalide (m/z 189.1) and human hepatic microsomes analyzed by LC-MS/MS. As shown in FIG. 1A, the most intense peaks (m/z) are 171.2 amu, 153.1 amu, 143.0 amu, 128.0, and 115.0 amu.

TABLE 1

Phase I metabolites

| Species | Metabolites | Biotransformation pathway | Mass-shifted peaks |
|---|---|---|---|
| Rat | Compound(2) | Dehydrogenation | m/z 189→187 |
|  | Compound(3); Compound(4) | Oxidation | m/z 189→205 |
|  | Compound(5); Compound(6); Compound (7) | Hydrogenation (forming hydrocarbyl group) | m/z 189→207 |
|  | Compound(8) | Tri-Demethylation | m/z 189→147 |
|  | Compound (9) | +Keto ($O_x$—2H) or methylation | m/z 189→203 |
| Dog | Compound(2) | Dehydrogenation | m/z 189→187 |
|  | Compound(3); Compound(4) | Oxidation | m/z 189→205 |
|  | Compound(5); Compound(6); Compound (7) | Hydrogenation (forming hydrocarbyl group) | m/z 189→207 |
|  | Compound(8) | Tri-Demethylation | m/z 189→147 |
|  | Compound(9) | +Keto ($O_x$—2H) or methylation | m/z 189→203 |
| Human | Compound(2) | Dehydrogenation | m/z 189→187 |
|  | Compound(3); Compound(4) | Oxidation | m/z 189→205 |
|  | Compound(5); Compound (6); Compound (7) | Hydrogenation (forming hydrocarbyl group) | m/z 189→207 |
|  | Compound(8) | Tri-Demethylation | m/z 189→147 |
|  | Compound(9) | +Keto ($O_x$—2H) or methylation | m/z 189→203 |

Figure 1B:
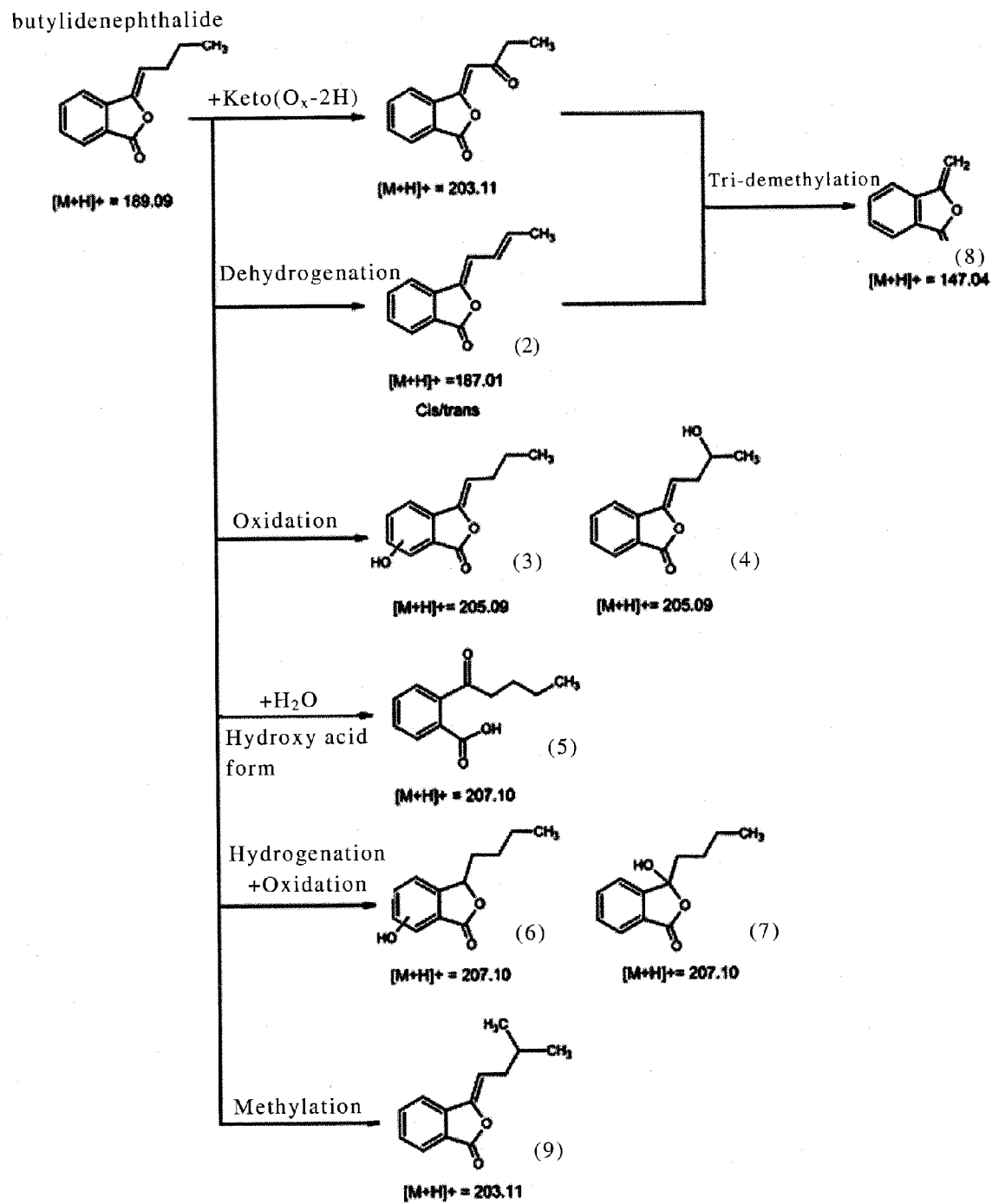
FIG. 1B is a metabolic profile showing the phase I metabolism of butylidenephthalide in an organism.

Table 1 shows the types of metabolites produced from the reaction of the mixture of butylidenephthalide and hepatic microsomes (i.e., phase I metabolism) and the biotransformation pathway acquired by software analysis. The results show that the compounds (2) to (9) of the present invention can be produced by the reaction of a mixture of butylidenephthalide and the hepatic microsomes of rat, dog or human, indicating that butylidenephthalide can be transformed to similar metabolites when metabolized in the livers of different organisms. FIG. 1B shows the metabolic profile obtained from the reaction of the mixture of butylidenephthalide and hepatic microsomes, and the chemical structures of compounds (2) to (9).

TABLE 2

Phase II metabolites

| Species | Metabolites | Biotransformation pathway | Mass shift |
|---|---|---|---|
| Rat | Compound(11) | +Cysteine | m/z 189→310 |
| | Compound(10) | +S-Glutathione | m/z 189→496 |
| | Compound(12) | Dehydrogenation + Sulfonation | m/z 189→267 |
| | Compound(13) | Glucoronidation | m/z 189→365 |
| Dog | Compound(11) | +Cysteine | m/z 189→310 |
| | Compound(10) | +S-Glutathione | m/z 189→496 |
| | Compound(13) | Glucoronidation | m/z 189→365 |
| | Compound(14) | Dehydrogenation + Oxidation +Glucose | m/z 189→365 |
| Human | Compound(11) | +Cysteine | m/z 189→310 |
| | Compound(10) | +S-Glutathione | m/z 189→496 |
| | Compound(12) | Dehydrogenation + Sulfonation | m/z 189→267 |
| | Compound(13) | +Glucoronidation | m/z 189→365 |

Figure 1C:
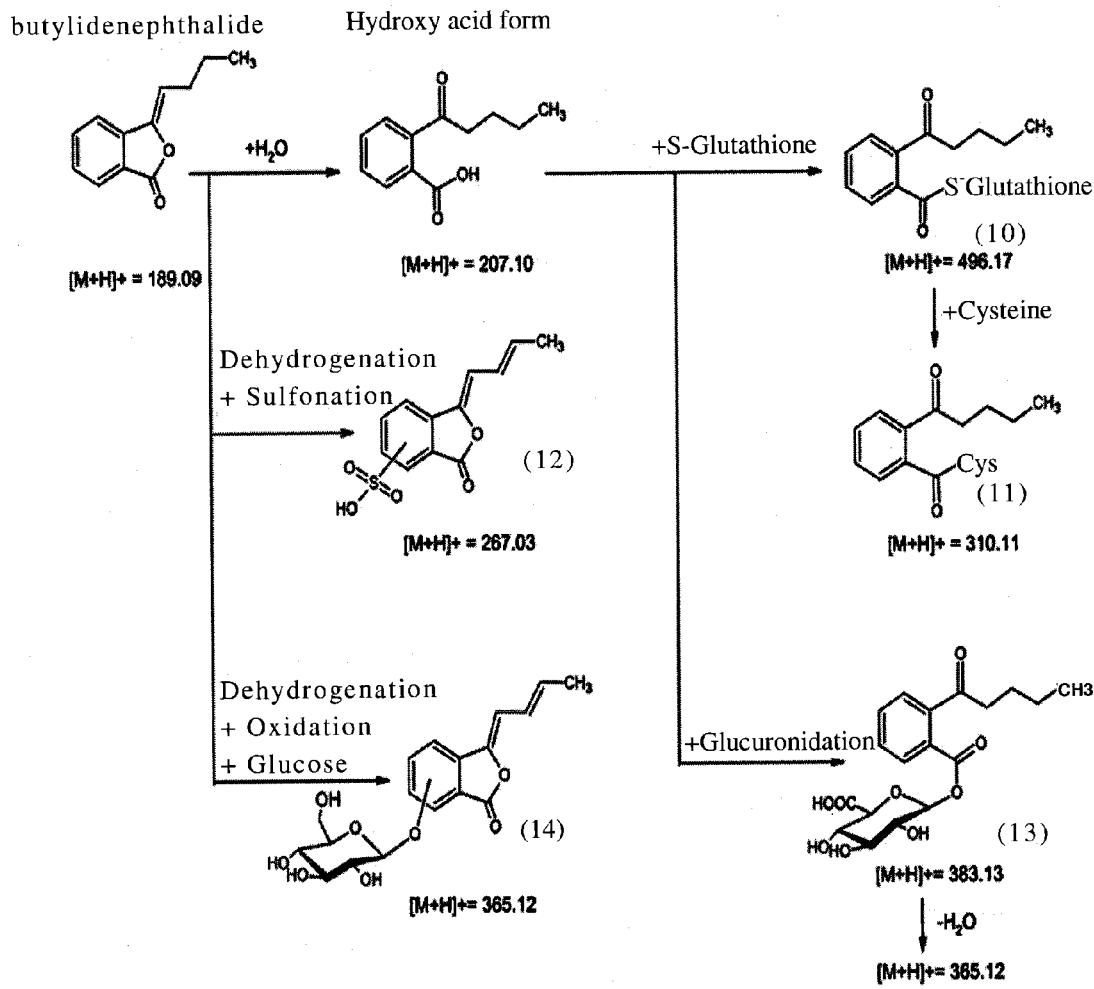
FIG. 1C is a metabolic profile showing the phase II metabolism of butylidenephthalide in an organism.

Table 2 shows the types of metabolites produced from the reaction of the mixture of butylidenephthalide and cryopreserved hepatocytes (i.e., phase II metabolism) and the biotransformation pathway acquired by software analysis. The results show that compounds (11) to (14) of the present invention can be produced by the reaction of a mixture of butylidenephthalide and the cryopreserved hepatocytes of rat, dog or human, indicating that butylidenephthalide can be transformed to similar metabolites when metabolized in the livers of different organisms. FIG. 1C shows the metabolic profile obtained from the reaction of the mixture of butylidenephthalide and cryopreserved hepatocytes, and the chemical structures of compounds (11) to (14).

Example 2

In vivo Analysis: Butylidenephthalide Increases the Survival Rate of Transgenic Mice It has been known that about 20% of amyotrophic lateral sclerosis patients were associated with mutations in the gene that encodes Cu/Zn superoxide dismutase enzyme (SOD1), and G93A was the major mutation site. The mice transfected with human mutant SOD1-G93A by gene transfection technique (hereafter referred to as SOD1-G93A transgenic mice) was used as an animal model for the clinical study of amyotrophic lateral sclerosis since the mice exhibit a similar course of disease to human. A SOD1-G93A transgenic mouse will show the symptoms of amyotrophic lateral sclerosis within about 90±5 days postnatal and will die within about 125±5 days postnatal.

This example used the above SOD1-G93A transgenic mice as the object of study to perform in vivo analysis. SOD1-G93A transgenic mice (60-day-old) were treated with butylidenephthalide (purchased from ECHO Chemical) by oral administration, with a dosage of 500 mg/kg-body weight once daily, wherein the unit "mg/kg-body weight" means the dosage required per kg-body weight. After the SOD1-G93A transgenic mice were treated for 30 days, they were observed to see if butylidenephthalide can lengthen the life of the SOD1-G93A transgenic mice (i.e., more than 125 days). The results are shown in FIG. 2 and Table 3.

TABLE 3

| | Survival days |
|---|---|
| Control group (n = 17) | 127 ± 6.11 |
| Experimental group (n-BP, 500 mg/kg-body weight) (n = 8) | 149 ± 4.39 |

Figure 2:
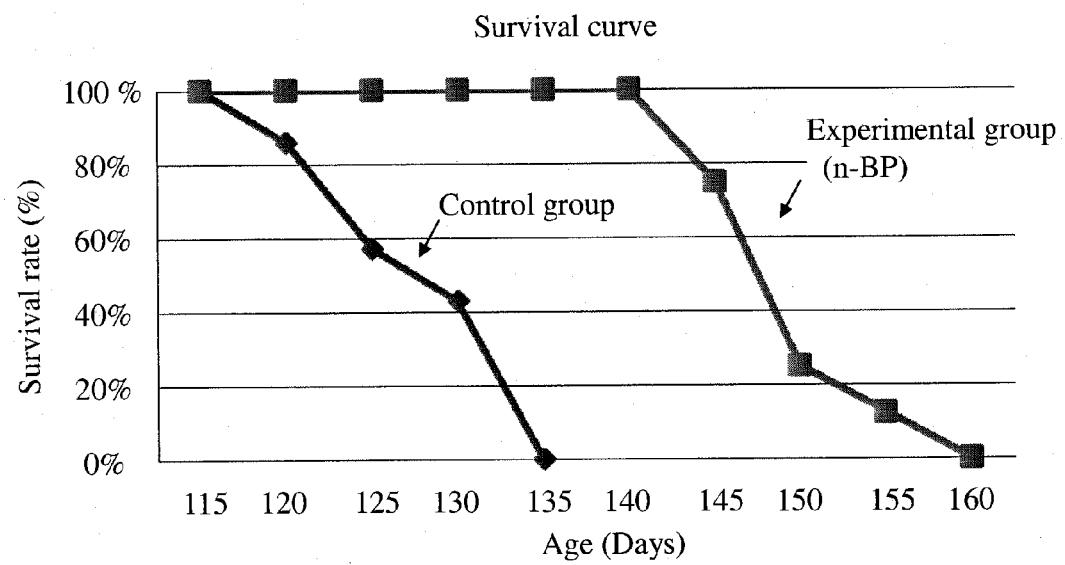
FIG. 2 is a survival curve diagram showing the effect of butylidenephthalide on increasing the survival rate of SOD1-G93A transgenic mice.
Figure 3:
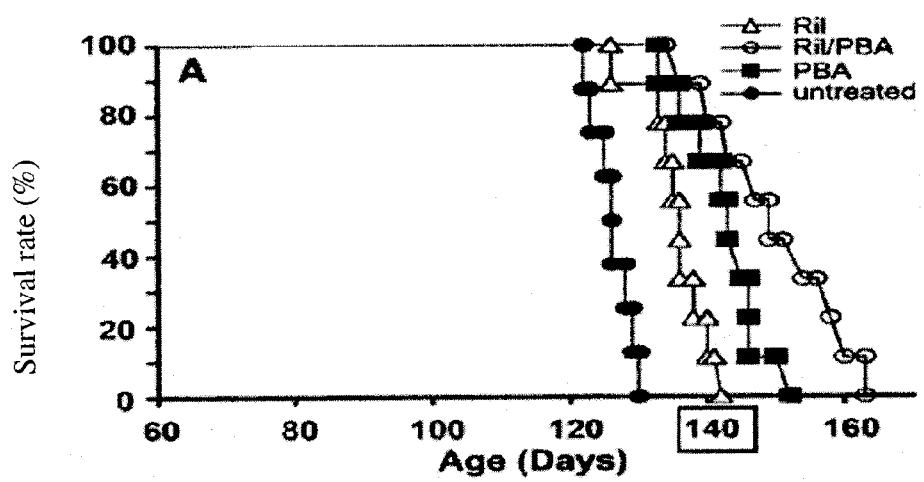
FIG. 3 is a survival curve diagram showing the effect of Riluzole on increasing the survival rate of SOD 1-G93A transgenic mice.

As shown in FIG. 2 and Table 3, the 60-day-old SOD1-G93A transgenic mice in the experimental group that were treated with butylidenephthalide by daily oral administration survived for about 149±4.39 days on average. That is, the life of the SOD1-G93A transgenic mice in experimental group was lengthened for about 22±2 days as compared to the untreated SOD1-G93A transgenic mice in the control group (survived for about 127±6.11). According to FIG. 3 (obtained from a reference "Combined riluzole and sodium phenylbutyrate therapy in transgenic amyotrophic lateral sclerosis mice. *Amyotrophic Lateral Sclerosis*. 2009; 10: 85-94," which is entirely incorporated hereinto by reference), when the traditional amyotrophic lateral sclerosis drug, Riluzole, was used to cure SOD1-G93A transgenic mice, the mice survived for 140 days. The above results show that as compared with Riluzole, the present invention using the compound of formula (I) can more effectively increase the survival rate of amyotrophic lateral sclerosis patients.

Example 3

In vivo Analysis: Butylidenephthalide Delays the Onset of Amyotrophic Lateral Sclerosis SOD1-G93A transgenic mice (60-day-old) were treated with butylidenephthalide by oral administration, with a dosage of 500 mg/kg-body weight once daily. After the mice were treated for 30 days, the hind limbs of the mice were examined by BBB scale (Basso, Beattie, and Bresnahan (BBB) Locomotor Rating Scale). The BBB scale of the hind limbs of normal mice was 21 points, while the BBB scale of disease-progressed SOD1-G93A transgenic mice decreased from 21 to 0 points, wherein the lower scale represents a more severe action disorder in the mice. BBB scale is used to record the drug efficiency.

Figure 4:
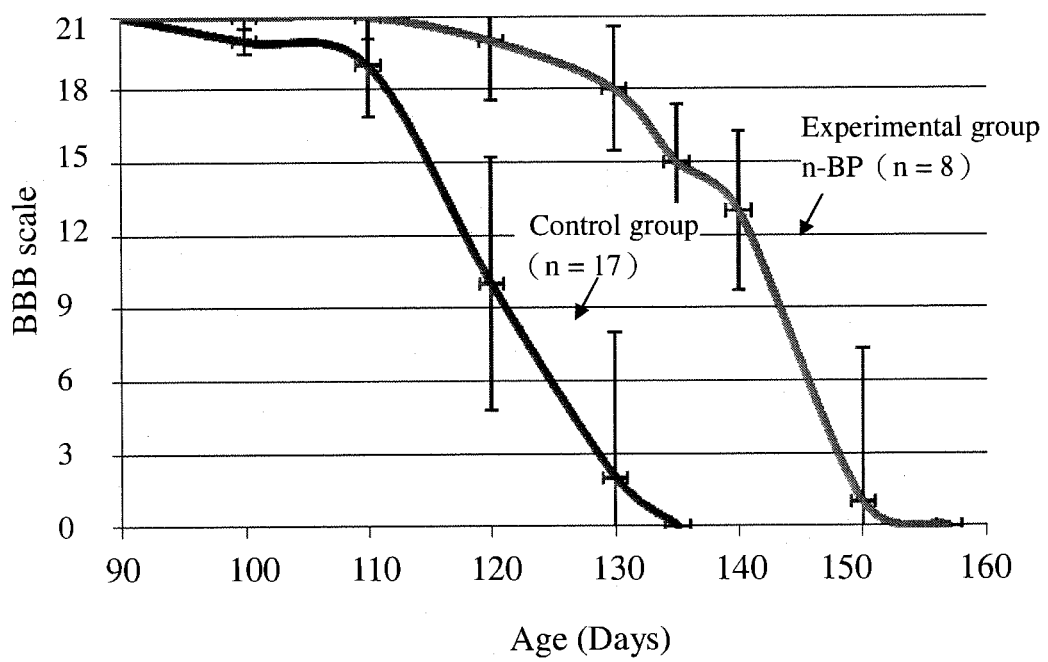
FIG. 4 is a BBB-scaled curve showing the effects of butylidenephthalide on the SOD1-G93A transgenic mice.

As shown in FIG. 4, the 60-day-old SOD1-G93A transgenic mice in the experimental group were treated with butylidenephthalide by daily oral administration. The BBB scale of the hind limbs of the mice decreased slowly from 125 to 135 days (from 21 to 16 points), and decreased rapidly after 135 days (from 16 to 0 points); while the BBB scale of the hind limbs of the untreated mice in the control group decreased rapidly after 110 days (from 19 to 0 points). The above results showed that butylidenephthalide can actually delay the onset of amyotrophic lateral sclerosis.

Example 4

Histochemical Staining: Butylidenephthalide can Delay and/or Prevent Spinal Motor Neuronal Death SOD1-G93A transgenic mice (60-day-old) were treated with butylidenephthalide by oral administration, with a dosage of 500 mg/kg-body weight once daily. The SOD1-G93A transgenic mice in the experimental group were sacrificed in extremis, and the spinal cord was collected to perform hematoxylin and eosin stain. The number of motor neurons in the spinal cord was observed and counted by using a microscope, and the data was compared with that of the untreated control group.

Figure 5A:
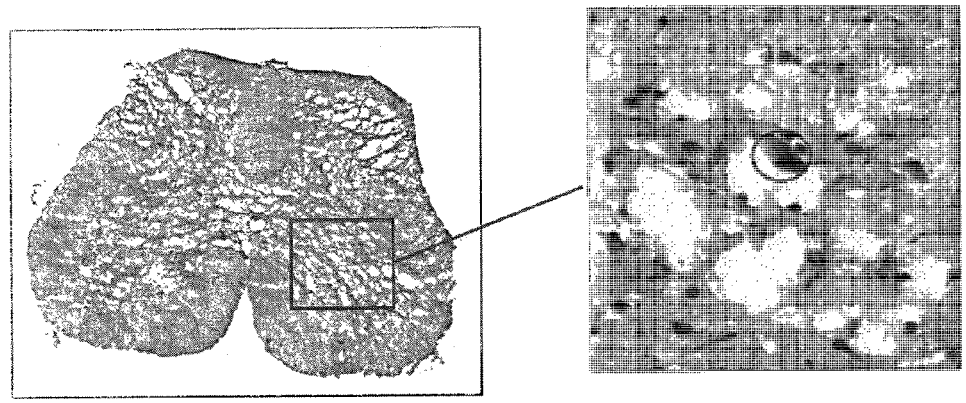
FIG. 5A is a histochemical staining picture showing the effects of butylidenephthalide on delaying or preventing the spinal motor neuronal death of SOD 1-G93A transgenic mice.
Figure 5A:
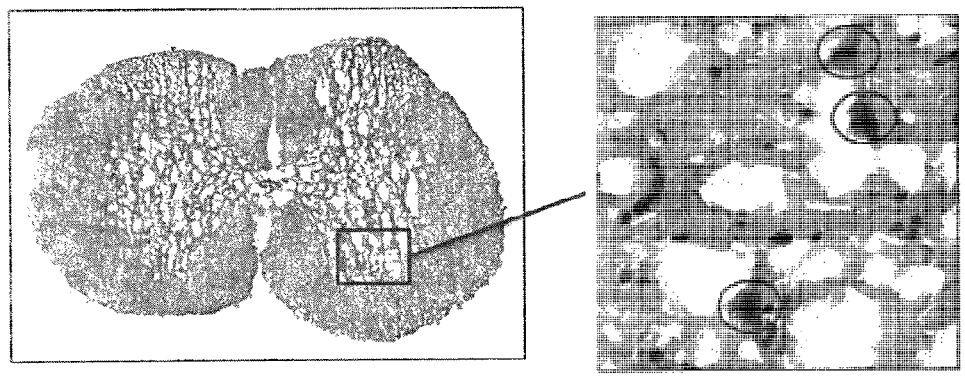
Figure 5B:
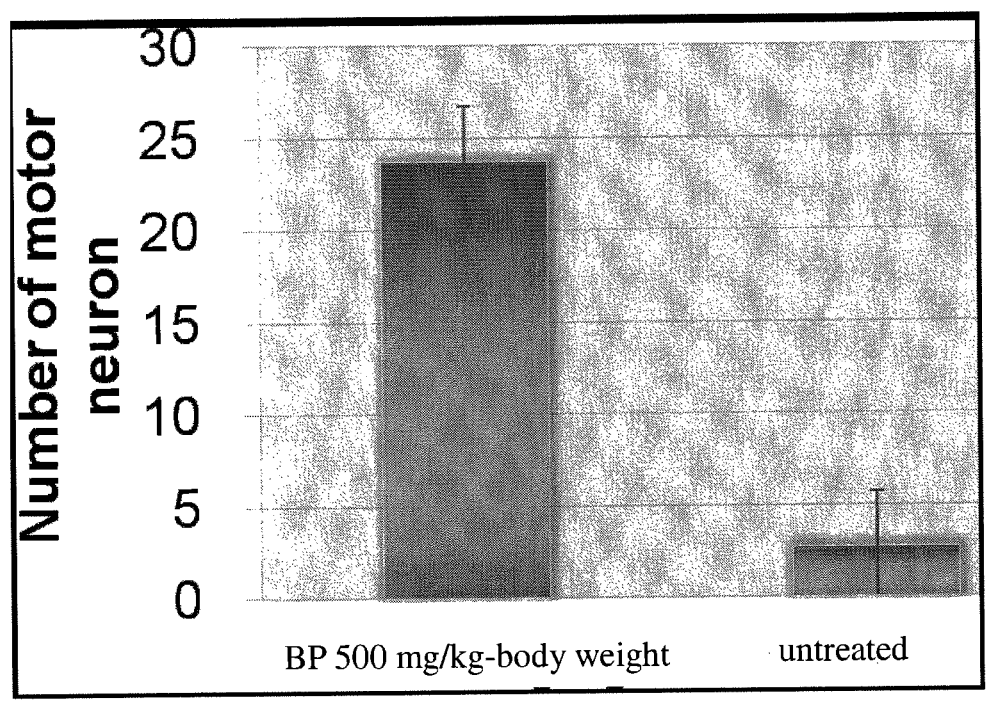
FIG. 5B is a bar diagram showing the effects of butylidenephthalide on delaying or preventing the spinal motor neuronal death of SOD1-G93A transgenic mice.

As shown in FIG. 5A, FIG. 5B and Table 4, the number of the spinal motor neurons of the 60-day-old SOD1-G93A transgenic mice in experimental group treated with butylidenephthalide everyday was significantly higher than that of control group (the number of the experimental group: 24; the number of the control group: 3). The above results show that butylidenephthalide can effectively delay and/or prevent spinal motor neuronal death, thereby, increasing the survival rate of SOD1-G93A transgenic mice.

TABLE 4

|  | The number of motor neurons |
|---|---|
| Control group | 3 ± 3.1 |
| Experimental group (n-BP, 500 mg/kg-body weight) | 24 ± 4.2 |

Example 5

Western Blotting Analysis: Butylidenephthalide can Inhibit Autophagy

SOD1-G93A transgenic mice (60-day-old) were treated with butylidenephthalide by oral administration, with a dosage of 500 mg/kg-body weight once daily. It has been indicated by research that SOD1-G93A transgenic mice lost its spinal motor neurons because of the significant increase of autophagy during the last phase of amyotrophic lateral sclerosis (which can be seen in In vivo optical imaging of motor neuron autophagy in a mouse model of amyotrophic lateral sclerosis. *Autophagy* 7:9, 1-8; September 2011, which is entirely incorporated hereinto by reference). Therefore, in this example, the SOD1-G93A transgenic mice in experimental group were sacrificed in extremis to collect their spinal cord, and the proteins were extracted from the spinal cord to perform Western blotting and to analyze the protein biomarker of autophagy, LC3-II, which was used to determine whether autophagy occurred in the lumbar spinal motor neurons of the mice, wherein β-actin was used as an internal control.

Figure 6:
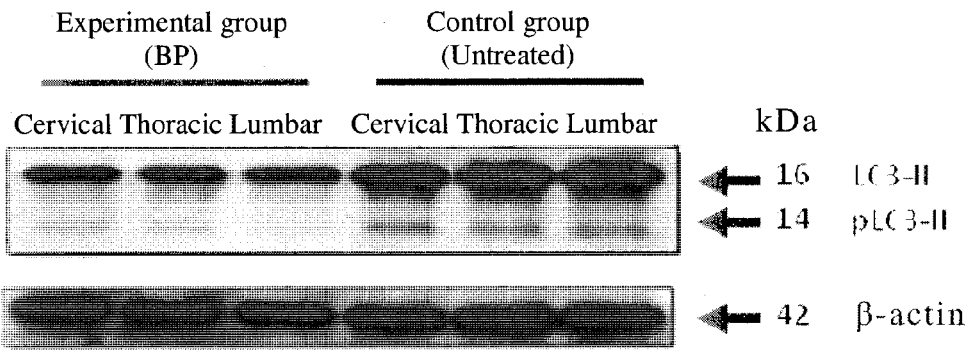
FIG. 6 is a Western blot picture showing the effect of butylidenephthalide on decreasing the expression level of LC3-II protein in the lumbar spine of SOD1-G93A transgenic mice.

As shown in FIG. 6, as compared with the untreated mice in control group, the protein expression level of LC3-II and pLC3-II in the cervical spinal cord, thoracic spinal cord, and lumbar spinal cord of the mice in experimental group were significantly decreased. The above results show that butylidenephthalide can specifically inhibit the autophagy of motor neurons in the organism, and thereby, delay the onset of amyotrophic lateral sclerosis, lengthen the survival days of the mice, and achieve the effect of curing amyotrophic lateral sclerosis.

Example 6

Cellular Experiment: Butylidenephthalide can Inhibit Autophagy

Cellular experiment was performed by using NSCs (neural stem cells) which can differentiate into mouse motor neurons to imitate mouse motor neurons.

NSCs were incubated in a culture dish (10 cm in diameter). The cells were washed with PBS when grown to a density of 60% confluence, and treated with different concentrations of butylidenephthalide for 12 hours. The cells were then treated with $H_2O_2$ (2500 μM/mL) for 12 hours to stimulate the autophagy of cells. Then, the cells were collected and the proteins were extracted, and the protein expression level of LC3-II in NSC was analyzed by SDS-PAGE and Western blotting. The result of Western blotting is shown in FIG. 7.

Figure 7:
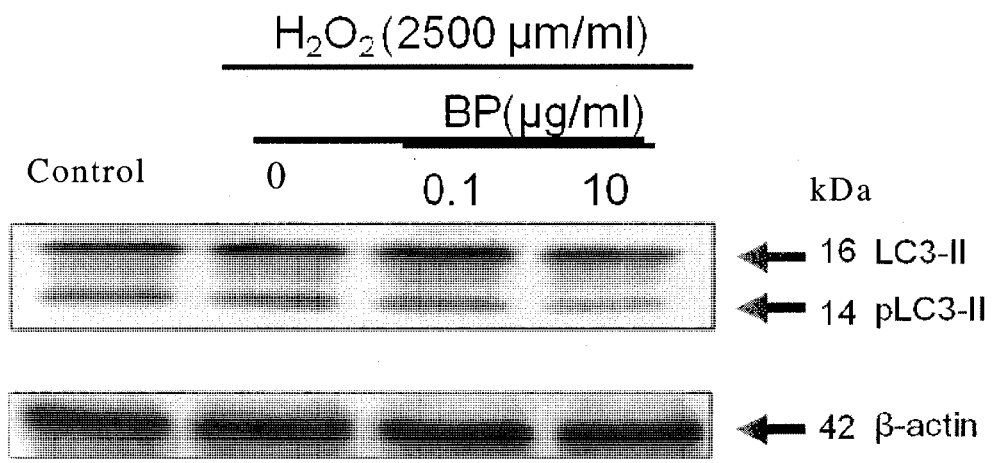
FIG. 7 is a Western blot picture showing the effect of butylidenephthalide on inhibiting the autophagy of NSC.

As shown in FIG. 7, 10 μg/mL butylidenephthalide can protect and prevent NSCs from $H_2O_2$ damage by inhibiting autophagy (decrease the protein expression level of LC3-II).

The above examples are used to illustrate the principle and efficacy of the present invention and show the inventive features thereof. People skilled in this field may proceed with a variety of modifications and replacements based on the disclosures and suggestions of the invention as described without departing from the principle and spirit thereof. Therefore, the scope of protection of the present invention is that as defined in the claims as appended.

What is claimed is:

1. A method for inhibiting the autophagy of motor neurons in a subject suffering from undesired autophagy of motor neuron, comprising administering to the subject an effective amount of an active component selected from the group consisting of butylidenephthalide (BP) a pharmaceutically acceptable salt of BP, and combinations thereof.

2. The method as claimed in claim 1, wherein the BP is (Z)-BP.

3. The method as claimed in claim 1 for inhibiting the autophagy of spinal motor neurons.

4. The method as claimed in claim 1, wherein the active component is administered at an amount ranging from about 30 mg (as BP)/kg-body weight to about 2,000 mg (as BP)/kg-body weight per day.

5. The method as claimed in claim 4, wherein the active component is administered at an amount ranging from about 100 mg (as BP)/kg-body weight to about 1,000 mg (as BP)/kg-body weight per day.

6. A method for treating and/or delaying the onset of amyotrophic lateral sclerosis in a subject in need of such treatment, comprising administering to the subject an effective amount of an active component selected from the group consisting of BP, a pharmaceutically acceptable salt of BP and combinations thereof.

7. The method as claimed in claim 6, wherein the BP is (Z)-BP.

8. The method as chimed ha claim 6, wherein the active component is administered at an amount ranging from about 30 mg (as BP)/kg-body weight to about 2,000 mg (as BP)/kg-body weight per day.

9. The method as claimed in claim 8, wherein the active component is administered at an amount ranging from about 100 mg (BP)/kg-body weight to about 1,000 mg (as BP)/kg-body weight per day.

* * * * *